(12) United States Patent
Cox

(10) Patent No.: US 8,220,347 B2
(45) Date of Patent: Jul. 17, 2012

(54) DEVICE FOR USE WITH MEASURING SOIL GAS AND METHOD OF USE

(75) Inventor: Craig A. Cox, Columbus, OH (US)

(73) Assignee: Cox-Colvin & Associates, Inc., Plain City, OH (US)

( * ) Notice: Subject to any disclaimer, the term of this patent is extended or adjusted under 35 U.S.C. 154(b) by 0 days.

(21) Appl. No.: 13/230,935

(22) Filed: Sep. 13, 2011

(65) Prior Publication Data

US 2012/0000298 A1 Jan. 5, 2012

Related U.S. Application Data

(63) Continuation-in-part of application No. 12/773,772, filed on May 4, 2010.

(51) Int. Cl.
*G01N 1/22* (2006.01)
(52) U.S. Cl. .............. 73/866.5; 73/863.71; 73/863.81; 73/864.81
(58) Field of Classification Search ............ 73/863, 73/863.81, 864.81, 866.5, 863.71
See application file for complete search history.

(56) References Cited

U.S. PATENT DOCUMENTS

| | | | | |
|---|---|---|---|---|
| 2,141,261 A | * | 12/1938 | Clark | 73/864.61 |
| 3,343,421 A | * | 9/1967 | Miller | 73/864.34 |
| 3,379,461 A | | 4/1968 | Davis | |
| 3,490,288 A | * | 1/1970 | Patnode | 73/863.23 |
| 3,610,048 A | * | 10/1971 | Weeks | 3/863.23 |
| 3,711,130 A | | 1/1973 | Betzler | |
| 3,783,804 A | * | 1/1974 | Platz | 111/7.4 |
| 4,020,697 A | * | 5/1977 | Jander | 73/864.73 |
| 4,146,254 A | | 3/1979 | Turner et al. | |
| D254,505 S | * | 3/1980 | Parsons et al. | D23/262 |
| 4,261,203 A | * | 4/1981 | Snyder | 73/864.74 |
| 4,310,057 A | * | 1/1982 | Brame | 175/21 |
| 4,335,622 A | * | 6/1982 | Bartz | 73/864.74 |
| 4,350,051 A | * | 9/1982 | Thompson | 73/864.74 |
| 4,452,091 A | * | 6/1984 | Richers | 73/864.52 |
| 4,524,608 A | * | 6/1985 | Bellefeuille et al. | 73/40.5 R |
| 4,603,890 A | | 8/1986 | Huppee | |
| 4,804,050 A | * | 2/1989 | Kerfoot | 175/20 |
| 4,951,976 A | | 8/1990 | Boelkins | |
| 4,969,879 A | | 11/1990 | Lichte | |
| 5,150,622 A | * | 9/1992 | Vollweiler | 73/864.74 |
| 5,176,411 A | | 1/1993 | DuPont, Jr. | |
| D333,178 S | * | 2/1993 | Novy | D23/262 |
| 5,330,235 A | * | 7/1994 | Wagner et al. | 285/81 |
| 5,403,046 A | * | 4/1995 | Kooten | 285/319 |
| D371,331 S | * | 7/1996 | Mooradian | D12/114 |
| 5,624,139 A | * | 4/1997 | Van Kooten | 285/31 |
| 5,711,551 A | * | 1/1998 | Miyazaki et al. | 285/136.1 |
| 5,786,527 A | * | 7/1998 | Tarte | 73/19.01 |
| 5,922,950 A | * | 7/1999 | Pemberton et al. | 73/152.28 |
| 6,152,495 A | * | 11/2000 | Hoffmann et al. | 285/148.19 |
| 6,230,820 B1 | * | 5/2001 | Cordry | 175/20 |
| 6,289,714 B1 | * | 9/2001 | Tartre | 73/19.01 |

(Continued)

*Primary Examiner* — David Rogers

(74) *Attorney, Agent, or Firm* — Standley Law Group LLP

(57) ABSTRACT

Exemplary embodiments are directed to a device and method of use thereof for facilitating the analysis of samples of sub-slab soil gas that comprise an adapter body that includes, a first barbed portion, an external engaging portion, a threaded collar portion, a second barbed portion, and an internal cavity that axially passes through the length of the adapter body. The device may further include a tubular body with an interior cavity adapted to receive at least a portion of the second barbed portion of the adapter body to produce a mating engagement therebetween.

18 Claims, 9 Drawing Sheets

U.S. PATENT DOCUMENTS

| | | | |
|---|---|---|---|
| 2001/0035057 A1* | 11/2001 | Jackson et al. | 73/863.83 |
| 2002/0043802 A1* | 4/2002 | Koster | 285/242 |
| 2003/0196498 A1* | 10/2003 | Hubbell et al. | 73/863.23 |
| 2004/0177672 A1* | 9/2004 | Schmitt et al. | 73/19.1 |
| 2006/0196114 A1* | 9/2006 | Allen | 47/48.5 |
| 2008/0028826 A1* | 2/2008 | Schmitt et al. | 73/19.01 |

* cited by examiner

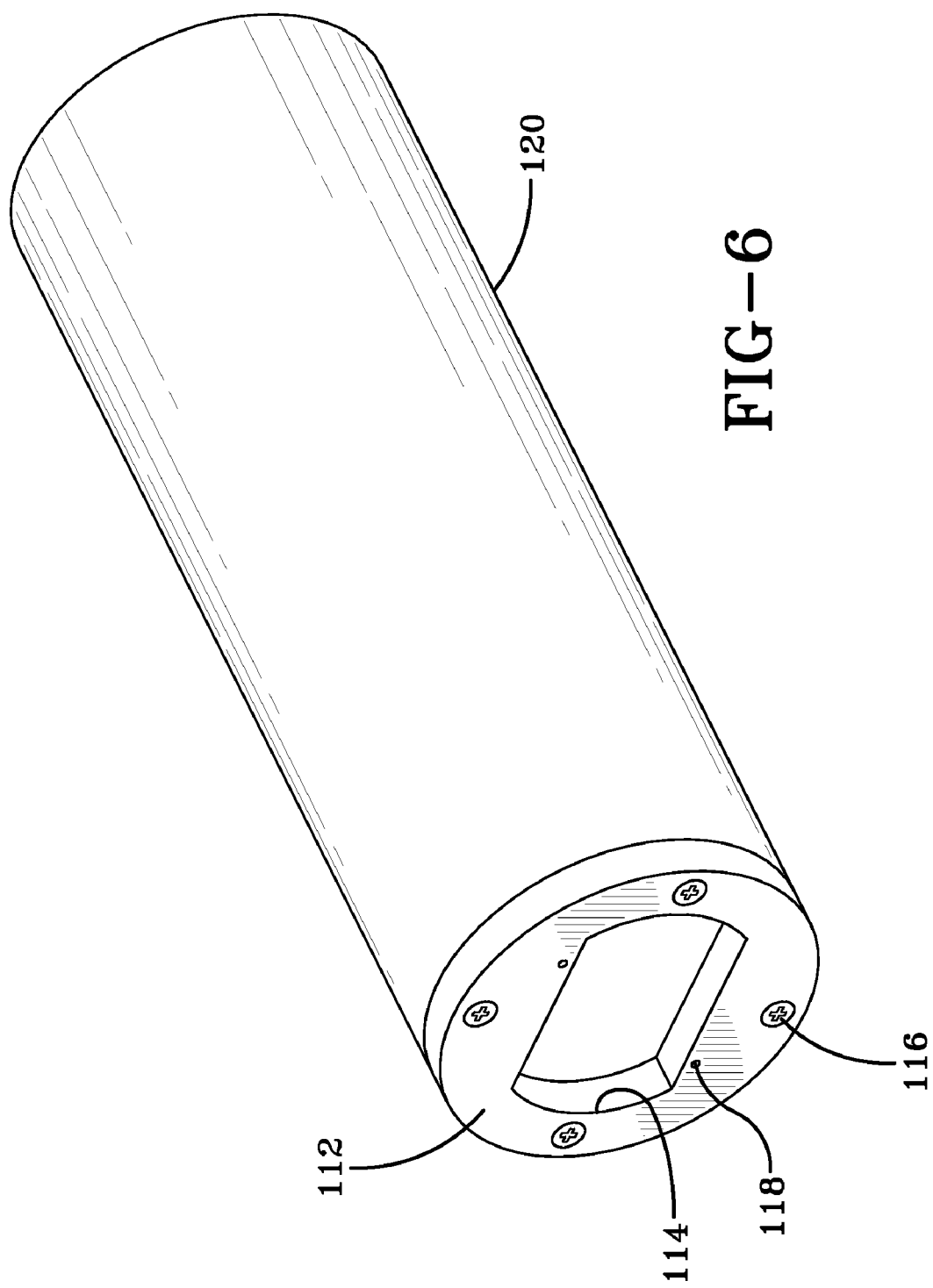

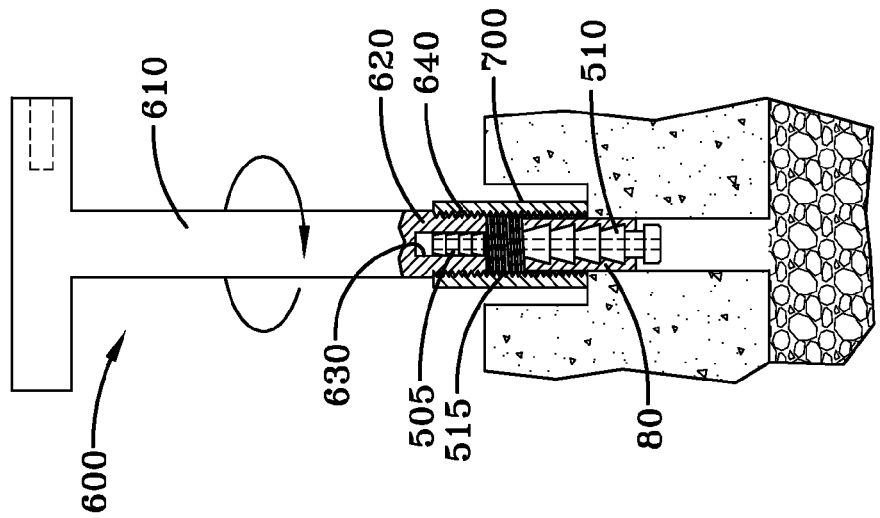
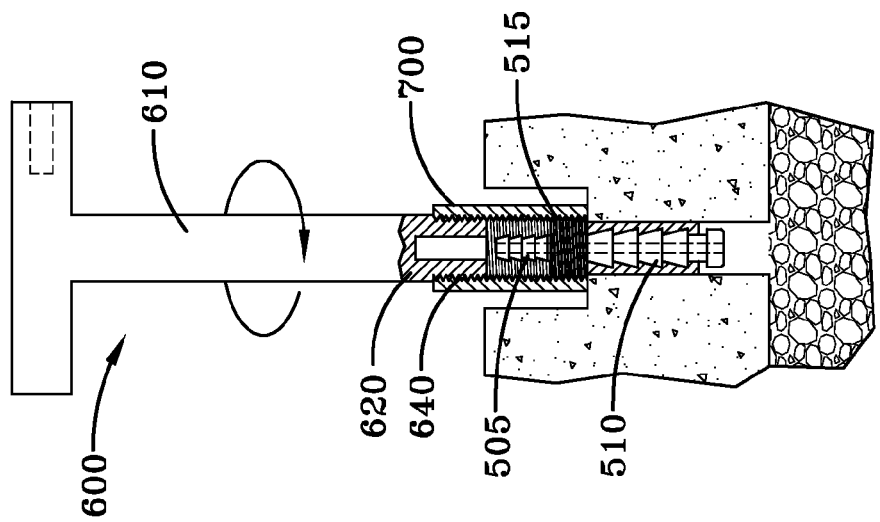

DEVICE FOR USE WITH MEASURING SOIL GAS AND METHOD OF USE

CROSS-REFERENCE TO RELATED APPLICATION

This application is a continuation-in-part of U.S. application Ser. No. 12/773,772 filed May 4, 2010, which is hereby incorporated by reference, as if fully rewritten herein.

INVENTIVE FIELD

Exemplary embodiments are directed to a device and method for analyzing gas levels. More particularly, exemplary embodiments are directed to a device and method of use thereof for facilitating the analysis of samples of sub-slab soil gas.

BACKGROUND

The potential for volatile organic compounds (VOCs) associated with contaminated soil and groundwater to enter homes and businesses through basements and building slabs is a recent focus of federal and state environmental protections agencies. This potential route of exposure is commonly referred to as the "vapor intrusion pathway." Evaluations of the potential risk associated with long-term exposure to VOCs have been published by the United States Environmental Protection Agency (EPA) and other entities. These evaluations indicate that very low concentrations of some of these VOCs, on the order of a few parts per billion in some cases, can pose an unacceptable risk to building occupants. In some situations, sub-slab soil gas samples are collected to evaluate vapor concentrations and the potential for these vapors to enter a building.

The science of analyzing samples of sub-slab soil gas is known. However, the practicalities of collecting these samples of gas are quite cumbersome. Techniques and devices currently used and proposed in recent draft guidance documents by the EPA and other agencies to collect sub-slab soil gas samples are built upon the experience of environmental professionals gained over many years of sampling groundwater via monitor wells. In essence, the current state of the art for sub-slab sampling is the use of a miniature well installed through the slab. These wells, or "sub-slab vapor points" are typically installed by boring a fairly crude hole through the slab and cementing a metal tube in place. At the top of the tube are a number of threaded fittings that allow the vapor point to be connected via plastic tubing to an evacuated vessel, known in the art as a summa canister.

Because the levels of concern for many of the VOCs are so low, leaks in the vapor point fittings or along the edge of the vapor point itself allow indoor air to dilute the sample, rendering the sample useless. This situation is exacerbated by the fact that most vapor points must be sampled on multiple occasions. Each time the vapor point is used it must be disconnected and reconnected using multiple wrenches, usually in tight quarters. This activity can cause some fittings to progressively loosen and leak more readily, or result in the point itself losing its bond with the cement used to anchor it during installation. Federal and state EPA officials recognize this shortcoming and have developed elaborate, time consuming methods for detecting such leaks.

However, the collection of sub-slab samples can still be inconvenient to building occupants since it requires the removal of floor coverings and coring or drilling of the foundation slab. One recommended method using an electric hammer drill or rotary hammer to produce an inner pilot hole into the concrete slab. After the pilot hole is drilled, an individual must drill an outer hole to a predetermined depth using a larger drill bit. After the outer hole is finished, the individual must use the original tool to assure that the pilot hole is then drilled through the slab and several inches into the sub-slab material. Once the drilling is completed, a stainless steel probe is assembled and inserted into the pre-drilled hole. The probe is mounted as flush as possible with the surrounding slab to minimize the interference with pedestrian or vehicular traffic. The probe has to be cemented into place to encourage that the probe assembly is air-tight with the foundation slab. Since the cement has to cure, an individual must come back at least one further time before sampling of the sub-soil may occur, further inconveniencing a homeowner or business.

What is desired is a device and method of use thereof that eliminates some or all of the drawbacks of the known devices and techniques for measuring sub-slab soil gas. Providing a leak-resistant device that allows for prompt installation and removal, saving time and money may eliminate some or all of these drawbacks. Also, a device and method that allows for installation to occur in one appointment is desirable. Such a device may also be designed for use with different VOC measuring devices.

SUMMARY

Exemplary embodiments of the device may eliminate some or all of the aforementioned drawbacks of the current art. Exemplary embodiments of the device may be machined from a single piece material, such as brass, eliminating the need for multiple fittings and thereby reducing the number of potential leaks. Exemplary embodiments of the device may be installed into a one-inch diameter hole cored through the slab of concrete or other foundation material. The cored hole provides a smoother bonding surface and can be accomplished using a standard, hand-held coring machine. Exemplary embodiments of the device may be driven into the cored hole using a hammer or similar device. Installation of exemplary embodiments of the device force the flexible silicone tubing located on at least a portion of the exterior surface thereof against the interior wall of the cored hole, effectuating an air-tight, or almost air-tight, seal between the cored slab and the device. Exemplary embodiments of the device may then be connected to a portion of the sampling tubing via an air-tight barbed fitting.

An exemplary embodiment of the device may be associated with an automated installation device. Such a device may be robotic in nature, or may be another type of automated device. Alternatively, an exemplary embodiment of the device may be employed by an individual to manually install the device, such as by a hammer.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 6 is a perspective view of an exemplary embodiment of an installation tool;

FIG. 9 illustrates an exemplary tool being used to remove an exemplary adaptor tool; and FIG. 10 illustrates an exemplary tool being used to remove an exemplary adaptor tool.

DETAILED DESCRIPTION OF EXEMPLARY EMBODIMENT(S)

Figure 1:
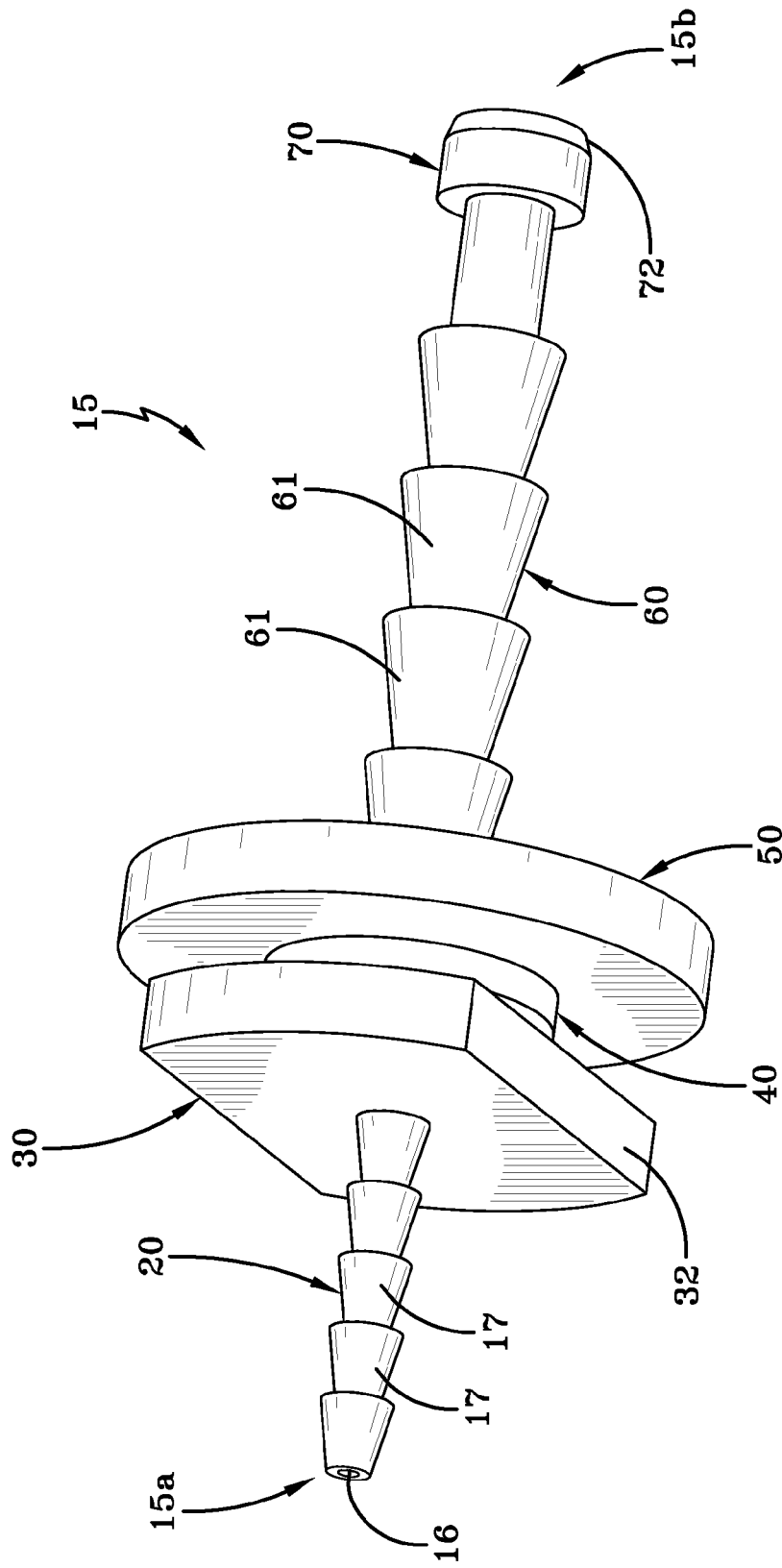
FIG. 1 is a perspective view illustrating one exemplary embodiment of an adapter body.

FIG. 1 depicts one exemplary embodiment of an adapter body of the device. As shown, this particular adapter body 15 of a device for use with measuring soil gas includes, a first barbed portion 20, an external engaging portion 30, a recess 40, a collar portion 50, a second barbed portion 60 and raised end 70.

Figure 2B:
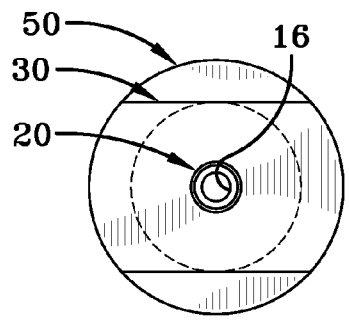
FIG. 2*b* is a top plan view of an exemplary embodiment of an adaptor body.
Figure 3B:
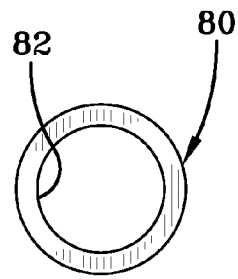
FIG. 3b is a top plan view of an exemplary embodiment of a tubing body.
Figure 2A:
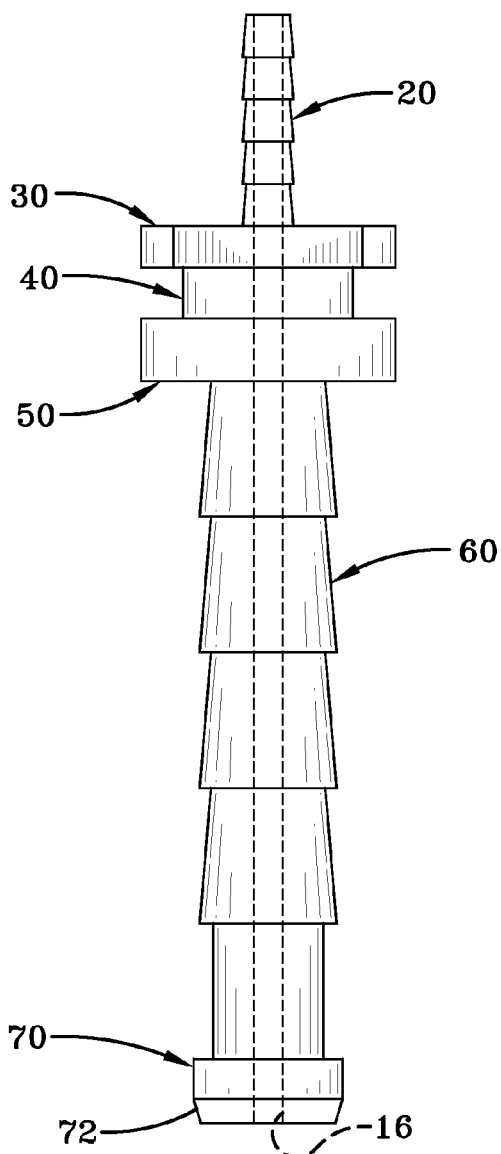
FIG. 2*a* is a front elevation view of an exemplary embodiment of an adaptor body.
Figure 3A:
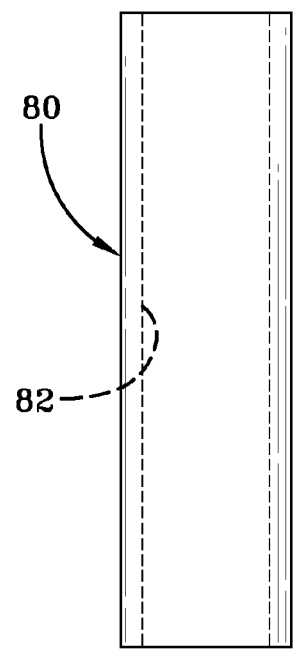
FIG. 3a is a front elevation view of an exemplary embodiment of a tubing body.

As shown in FIGS. 1-2b, the adapter body includes a proximal end 15a and a distal end 15b. Exemplary embodiments of the adapter body 15 may include a first barbed portion 20, an external engaging portion 30, a recess 40, a collar portion 50, a second barbed portion 60 and raised end 70. As seen in FIGS. 2a-2c, exemplary embodiments of the adapter body 15 may include an internal cavity 16 that axially passes through the length of the adapter body 15 from the proximal end 15a to the distal end 15b. The internal cavity 16 allows gas found in the subsoil to flow through the adapter body 15 and be read by a soil gas measuring device (not shown) that is connected with the adaptor body 15. The cross-sectional area and geometry of the internal cavity 16 may be substantially similar throughout the length of the adapter body 15.

In this embodiment, the first barbed portion 20 of the adapter body 15 is located towards the proximal end 15a thereof. The first barbed portion 20 generally includes at least one barb 17. In some examples, the barbs 17 are generally conical in geometry to facilitate the releasable securement of an exemplary embodiment of tubing (not shown) that connects the adaptor body 15 with a soil gas measuring device, such as a SUMMA canister. As such, the first barbed portion 20 may be manufactured from readily available sizes of round stock, thereby reducing manufacturing time and expense. However, it should be realized that the first barbed portion 20 may have any number of cross-sectional geometries, depending upon the cross-sectional geometry of the tubing that connects the device with the soil gas measuring device. Typically, the end-most barb located towards the proximal end 15a may include a generally rounded face that facilitates the insertion of the first barbed portion within the inner cavity of the tubing that connects the adaptor body 15 with a soil gas measuring device. In some exemplary embodiments, there are no gaps or land sections between the barbs 17. In such embodiments, the end of the barb with the smaller outside diameter may abut the next barb's end with the larger outside diameter.

Typically, when the barbs 17 bear a fixed dimensional relationship to the inside diameter of the tubing that connects the adaptor body 15 with a soil gas measuring device, the tubing will form a reliable pressure tight seal to the adaptor body 15. In one embodiment, the large diameter ends of the barbs 17 may be approximately 0.30", while the inner diameter of the tubing may be approximately 0.25". This type of press-fit may cause the tube to spread or flare so that after the first barbed portion 20 is fully inserted within the tube, the tube will return to its original size after releasable securement. Furthermore, in some embodiments, the conical shape of the barb 17, which is wider toward the point of insertion, provides a manner of anchoring the flexible tubing body 80 during the insertion process so that the tubing body 80 does not move in relation to the adapter body 15 during insertion.

The external engaging portion 30 of the adapter body 15 includes an external engaging portion, in this example, is a flange 32 adapted to engage a wrench or other tool. The external engaging portion 30 is shown here to be of substantially circular shape, wherein a portion of opposed sides are substantially parallel to one another. However, other shapes are also possible. In another example, the outside geometry of the external engaging portion 30 is substantially hexagonal or square in geometry to allow a user to engage thereto with a wrench or other tool. While this embodiment of the fastener engaging portion contains a flange, other embodiments may instead include a component, which allows for engagement with different tools, including a screwdriver head component, a hex head component, TORX head component, drill head component, or another engaging structure that can tighten and/or move the adaptor body 15 by rotational movement.

In some embodiments, the engaging portion 30 may be integral with the first barbed portion 20, such as by molding or turning. In other embodiments, the engaging portion 30 may be attached to the first barbed portion 20, such as by welding. Alternatively, the first barbed portion 20 may be removably attached to the engaging portion 30 so that the device 10 may be used with tubing of various size.

Figure 5A:
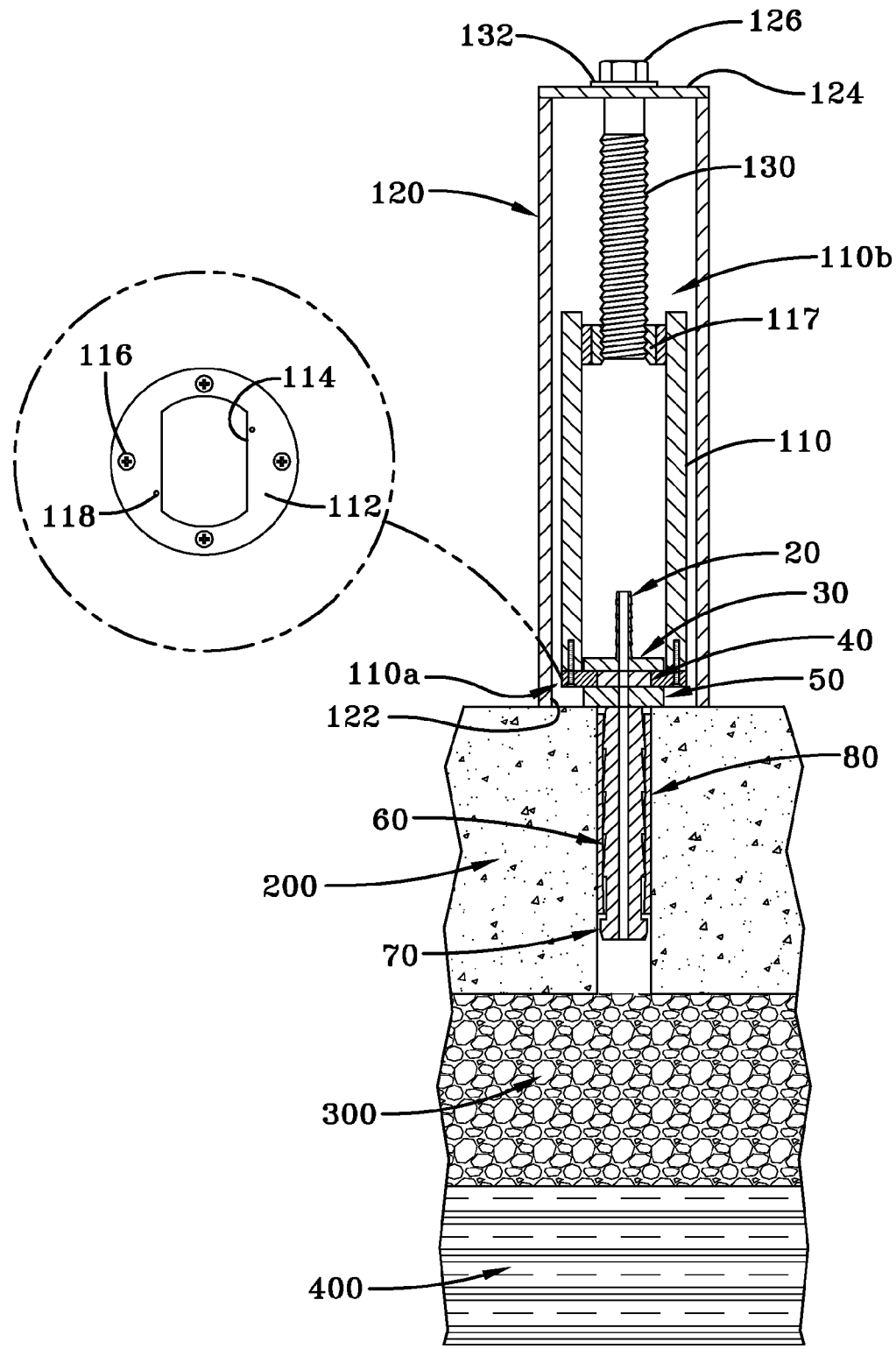
FIG. 5a is a cross-sectional view of an exemplary embodiment of the device with the installation tool prior to extraction.
Figure 5B:
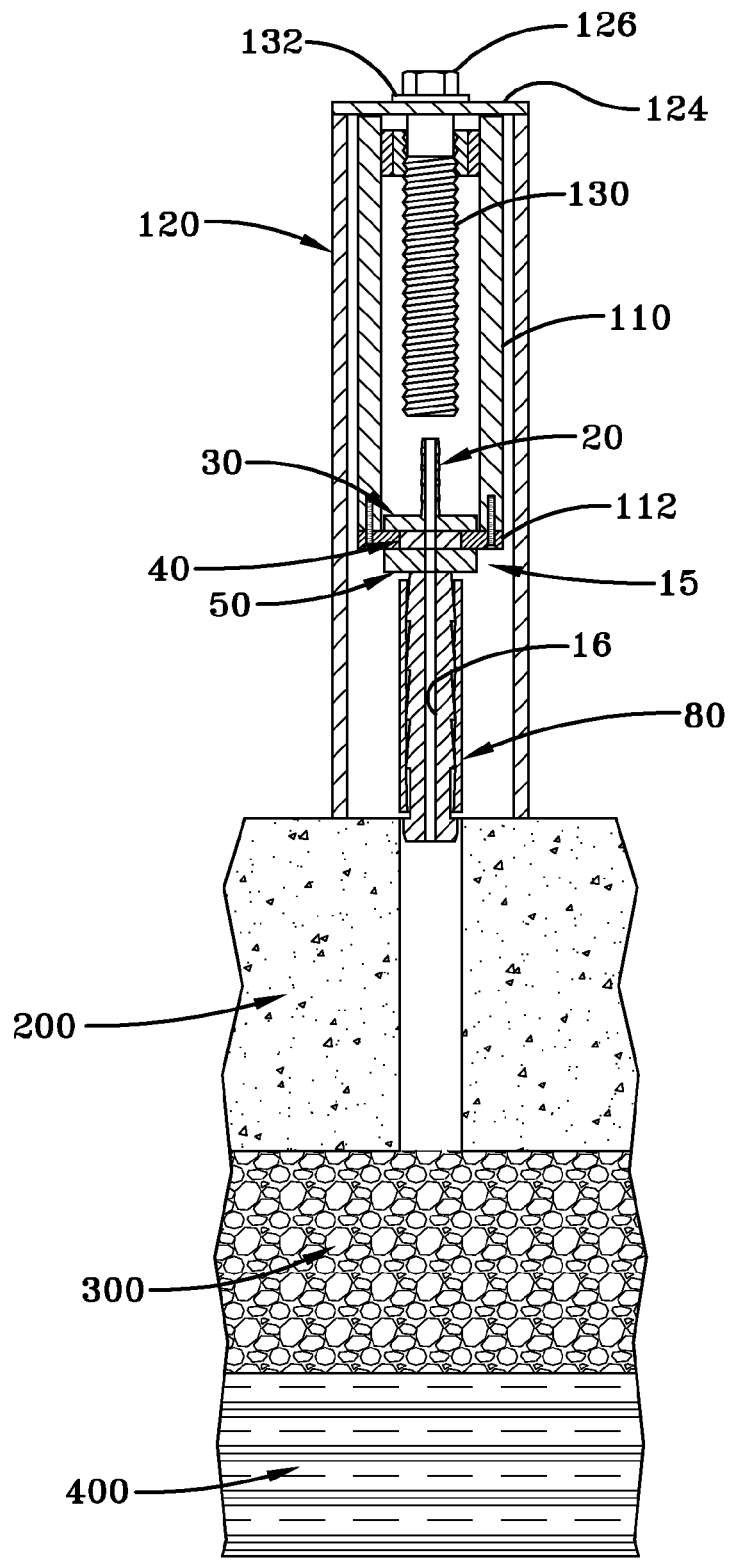
FIG. 5b is a cross-sectional view of an exemplary embodiment of the device with the installation tool after extraction has occurred.

In exemplary embodiments, the collar portion 50 is generally joined to the engaging portion 30 by an optional recess area 40 which has a generally cylindrical shape. The geometry of the recess area 40 may be of various cross-sectional areas, although a substantially round cross-sectional area may simplify manufacturing. The optional recess area 40 may also allow a wrench or other tool 100 to engage the engaging portion 30 and/or the collar portion 50 of the adaptor body 15 to facilitate the installation and/or removal of the adaptor body 15. In one example, as seen in FIGS. 5a and 5b, an individual may use the tool 100 to install and/or remove the device.

Figure 4:
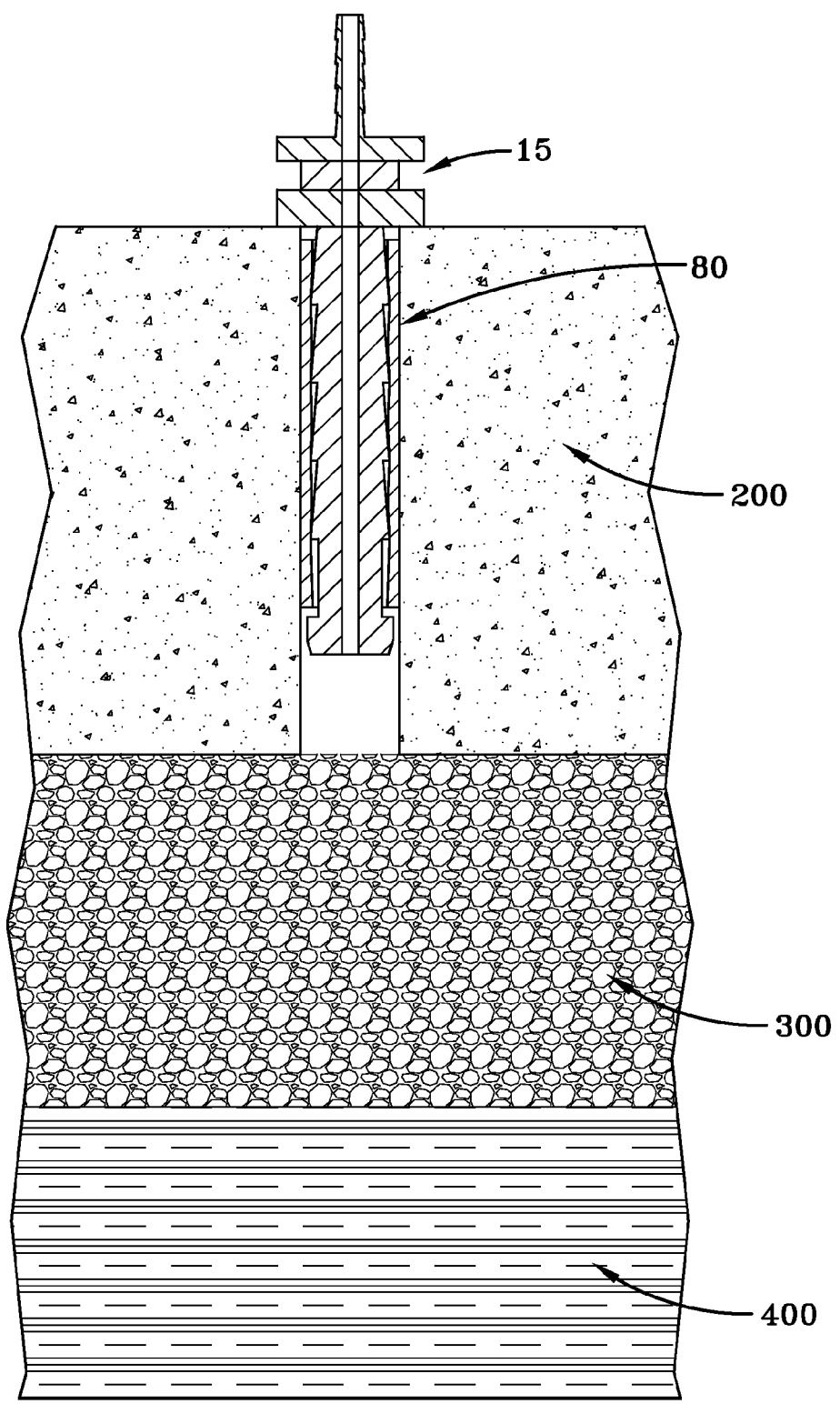
FIG. 4 is a cross-sectional view of an exemplary embodiment of the device installed within a foundation slab.

In this example, the entire collar portion 50 is substantially circular in cross-sectional geometry, wherein the diameter is substantially the same along the length thereof. The cross-sectional geometry of the collar section is typically substantially circular to facilitate the insertion of adapter body 15 within in a corresponding hole in the slab that is likewise substantially circular. However, in other embodiments, the collar portion 50 may also be of other cross-sectional shapes. As aforementioned, one of the main functions of the collar portion 50 is to provide a surface for a tool to contact the adapter body 15 for installation and/or removal of the adaptor body 15 during use. In some embodiments, during installation of the adaptor body 15, once the distal end of the collar portion 50 engages a portion of the slab, the device is fully engaged, as depicted in FIG. 4. In some embodiments, the collar portion 50 may taper inward (not shown) from a larger diameter as it extends longitudinally from the proximal end 15a of the adapter body 15. The taper may facilitate the securement of the tubular body 80 to the adapter body 15 during installation. In some embodiments, the collar portion 50 may be integral with the engaging portion 30, and the recess portion 40 such as by molding or turning. In other embodiments, the engaging portion 30 and the collar portion 50 may be attached to the recess portion 40, such as by welding.

As shown in the exemplary embodiment depicted in FIGS. 1-2b, the second barbed portion 60 of the adapter body 15 may be located towards the distal end 15b thereof. The second barbed portion 60 generally includes at least one barb 61. In some examples, the barbs 61 are generally conical in geometry to facilitate the releasable securement of the tubing body 80, as seen in FIG. 4. As such, the second barbed portion 60 may be manufactured from readily available sizes of round stock, thereby reducing manufacturing time and expense. However, it should be realized that the second barbed portion 60 may have any number of cross-sectional geometries, depending upon the cross-sectional geometry of the tubular body 80. Typically, the barbs 61 may taper from a larger diameter from the distal end 15b thereof. However, in other embodiments, some or all of the barbs 61 may taper from a larger diameter from the proximal end 15a thereof. In some exemplary embodiments, there are no gaps or land sections between the barbs 61. In such embodiments, the end of the barb with the smaller outside diameter may abut the next barb's end with the larger outside diameter.

Typically, when the barbs 61 bear a fixed dimensional relationship to the inside diameter of the tubular body 80 that will form a reliable pressure tight seal therebetween. In one embodiment, the large diameter ends of the barbs 61 may be approximately 0.79", while the inner diameter of the tubular body 80 may be approximately 0.75". This type of press-fit may cause the tube to spread or flare so that after the second barbed portion 60 is fully inserted within the tubular body 80, the tubular body 80 will return to its original size after releasable securement.

The exemplary embodiment raised end 70 of FIG. 1 can be seen in more detail in FIGS. 2a-2b. As shown, the raised end 70 is a substantially cylindrical shape, although other shapes are possible. This example of the raised end include a chamfer 72 or rounded end located at the distal end 15b of the adapter body 15, which facilitates the insertion of the raised end 70 within the inner cavity of the tubular body 80. Typically, but not necessarily, the outside diameter of the raised end 70 is approximately the same diameter of the largest diameter of the barbs 61. However, in other embodiments, the outside diameter of the raised end 70 may be greater or less than the outside diameter of the barbs 61.

The adapter body 15 may be made of any number of materials, such as, for example, brass, plastics, or other metals, such as stainless steel. Whatever material is selected, the resulting adapter body 15 should have sufficient strength to withstand the insertion and extraction of the adaptor body within the slab. Furthermore, it is preferred if the material is easy to manufacture, if machined.

As shown in FIG. 4, during installation the second barbed portion 60 and raised end 70 has disposed thereon a tubular body 80. The tubular body 80 may be any material that is flexible enough to allow securement of the tubular body around the second barbed portion 60 and the raised end 70, along with providing an air-tight seal between the adapter body 15 and the inside diameter of a hole drilled into the slab of a basement or foundation of a building. In one particular example, the tubular body 80 is fabricated from low-VOC content Silicone tubing, available from Dow-Corning. As aforementioned, the interior cavity 82 of the tubular body 80 is adapted to receive the raised end 70 and second barbed portion 60 of the adapter body 15 and may be of any shape required to produce mating engagement therebetween. Furthermore, in some embodiments one or more optional seals (not shown) may be placed around the barbs 61 of the second barbed portion 60 to help effectuate an air-tight seal between the tubular body 80 and the adapter body 15. It is also contemplated that the interior cavity of the tubular body 80 and/or the exterior of the second barbed portion 60 and/or raised end 70 may be coated or otherwise covered with a high friction material for facilitating the engagement therebetween. The length of the tubular body 80 may vary, depending upon the length between the collar portion 50 and the distal end 15b of the adapter body 15. In one example, the length of the tubular body 80 is approximately 3.75 inches. Likewise, the outside diameter of exemplary embodiments of the tubular body 80 may vary depending upon the inside diameter of the hole drilled or bored within the slab of concrete or other foundation of a building or other structure.

Particularly, in a normal assembled installation state, as seen in FIG. 4 the tubular body 80 is wedged between the second barbed portion 60 and/or the raised end 70, and the inside wall of the drilled or cored hole that extends through the foundation slab. In some methods of installation, the tubular body 80 is releasably secured around the second barbed portion 60 before the device is installed within the cored hole. In other embodiments, an installation tool 100, as seen in FIGS. 5a and 5b may apply pressure on a portion of the adaptor body 15 to effectuate installation within the cored hole.

During installation and/or extraction the tool 100 may include an inner body 110 that includes a contacting portion 112 at a first end 110a with an aperture 114 that complements the cross-sectional geometry as the engaging portion 30. In one example, the contacting portion 112 may be secured to the inner body 110 by one or more fasteners 116. However, in other examples the contacting portion 112 may be integral with the inner body 110 by welding, etc. The tool 100 may facilitate installation by allowing an individual to place the inner body 110 over and/or around the engaging portion 30 wherein at least a portion of the inner face of the contacting portion 112 of the tool 100 may contact the engaging portion 30 and/or at least a portion of the outer face of the contacting portion 112 may contact the collar portion 50 to allow the individual to strike a second portion of the tool 100 with a hammer or other object to facilitate installation of the adaptor body 15.

In other embodiments, an installation tool 100, as seen in FIGS. 5a and 5b may apply pressure on a portion of the adaptor body 15 to effectuate installation within the cored hole. In this embodiment, the contacting portion 112 may be positioned over and around the engaging portion 30, wherein at least a portion of the inner face of the contacting portions 112 of the tool 100 may contact the engaging portion 30 and/or at least a portion of the outer face of the contacting portion 112 may contact the collar portion 50 when the inner body 110 is turned approximately ninety degrees. In some examples, a surface of the contacting portion 112 or inner body 110 may including one or more raised surfaces 118 or other stopping device adapted to prohibit an individual from turning the inner body 110 of the tool 100 beyond a desired location, to effectuate contact with the device for installation and/or removal.

Exemplary embodiments of the inner body 110 are tubular in cross-sectional geometry. In some examples, it may be preferred that the inner body 110 is substantially cylindrical. The inner body 110 may include a threaded surface 117 located towards a second end 110b. The threaded surface 117 may be integral with the inner body 110, or may be a separate piece adhered to within or to the inner body 110. The threaded surface 117 is adapted to complement the threaded surface of a bolt or other threaded fastener 130, described later and seen in FIGS. 5a and 5b.

In some examples, the tool 100 may further include an outer body 120 that is tubular in cross-sectional geometry. In the example depicted in FIGS. 5a and 5b, the outer body 120 is substantially cylindrical in cross-sectional geometry to complement the geometry of the inner body 110. The first end of the outer body 120 contains an aperture 122 large enough to allow the outer body 120 to be positioned around the inner body 110.

Furthermore, some exemplary embodiments of the outer body 120 may include a top portion 124 with an aperture 126 located towards the second end thereof. In the example depicted in FIGS. 5a and 5b, the top portion 124 is a plate adhered to the second end of the outer body 120. However, in other embodiments, the top portion 124 may be optionally secured with the outer body 120 by fasteners or other securing devices.

During one exemplary method of extraction of the adaptor body 15, an individual may releasably secure the inner body 110 with the device as aforementioned. After the inner body 110 is secured with the adaptor body 15, the individual may position the outer body 120 around the inner body 110, as depicted in FIGS. 5a and 5b, wherein at least a portion of the outer body 120 engages the concrete slab 200. The individual places a bolt or other threaded fastener 130 down through the aperture 126 located towards the second end. An optional washer 132 or similar device may be used to help distribute the force exerted on the head of the threaded fastener 130. An individual may then rotationally engage the threaded fastener 130 with the complementary threaded surface 117, effectuating the removal of the device, as seen in FIG. 5b. The individual may use any number of tools or devices to rotate the bolt, and all of the devices are contemplated.

Likewise, the complementary portion of the tool 100 may be placed over and around the engaging portion 30, then rotated approximately ninety degrees so that the adaptor body 15 may be removed. In other embodiments, an installation tool 100, as seen in FIGS. 5a and 5b may apply pressure on a portion of the adaptor body 15 to effectuate installation and/or removal within the cored hole.

In some installation methods, the adaptor body is pressed downward in the cored hole until the collar engages the slab. However, some exemplary embodiments of the adaptor body may install wherein the adaptor body is mounted flush to accommodate a larger hole that is drilled deep enough to allow the first barbed portion to lie below the surface of the slab. In this exemplary embodiment, the entire adaptor body is mounted at least flush, if not below the surface level of the slab, decreasing the likelihood that the device may be damaged after installation. Installation of exemplary embodiments of the adaptor body may be installed into a one-inch diameter hole cored through the slab of concrete or other foundation material. The cored hole provides a smoother bonding surface and can be accomplished using a standard, hand-held coring machine. Exemplary embodiments of the adaptor body may be driven into the cored hole using a hammer or similar device.

Installation of exemplary embodiments of the adaptor body may force the flexible silicone tubular body located on at least a portion of the exterior surface thereof against the interior wall of the cored hole, effectuating an air-tight, or almost air-tight, seal between the cored slab and the device. Exemplary embodiments of the adaptor body may then be connected to a portion of the sampling tubing via an air-tight barbed fitting.

As mentioned above, it is also possible to manually install a device of the present invention within the foundation of a home, building or other surface that contains a foundation made of concrete or similar substance. Whether designed for manual or automatic operation, a device of the present invention may be associated with an automatic soil gas reading device (not shown). Such a soil gas reading device is operative to automatically read the VOC levels of the native material 400 such as soil and/or gravel backfill 300 contained under the foundation wherein exemplary embodiments of the device are installed, such as depicted in FIGS. 4-5b.

Figure 7:
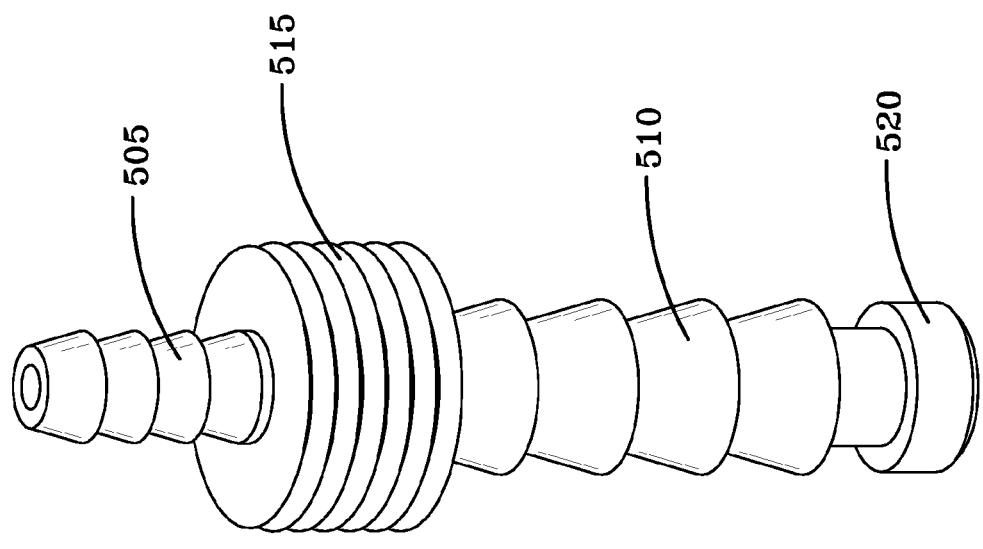
FIG. 7 is a front perspective view of an exemplary embodiment of an adaptor body according to the inventive concept.

FIG. 7 illustrates another exemplary embodiment of an adaptor body 15. In this embodiment, the adaptor body 500 has a first barbed end 505 and second barbed end 510. The adaptor body also has a male threaded collar 515 separating the first barbed portion 505 and the second barbed portion 510. A raised end 520 is provided at the distal end of the second barbed portion 510. As discussed herein, the first barbed portion 505 is sized and adapted to facilitate a connection between the adaptor body and a soil gas measuring device (not shown). The second barbed portion 510 is sized and adapted for insertion into a tube 80. The adaptor body 500 may have a unitary design or it may be constructed of modular sections. A modular construction would allow the first and second barbed portions 505, 510 and the threaded collar 515 to be changed to accommodate different sized components giving the adaptor body 500 greater flexibility. The adaptor body 500 may be made of brass or other material sufficiently strong to withstand the installation and extraction process. To allow soil gas samples to be taken, the adaptor body 500 has an internal passageway through which the soil gas may travel.

Figure 8:
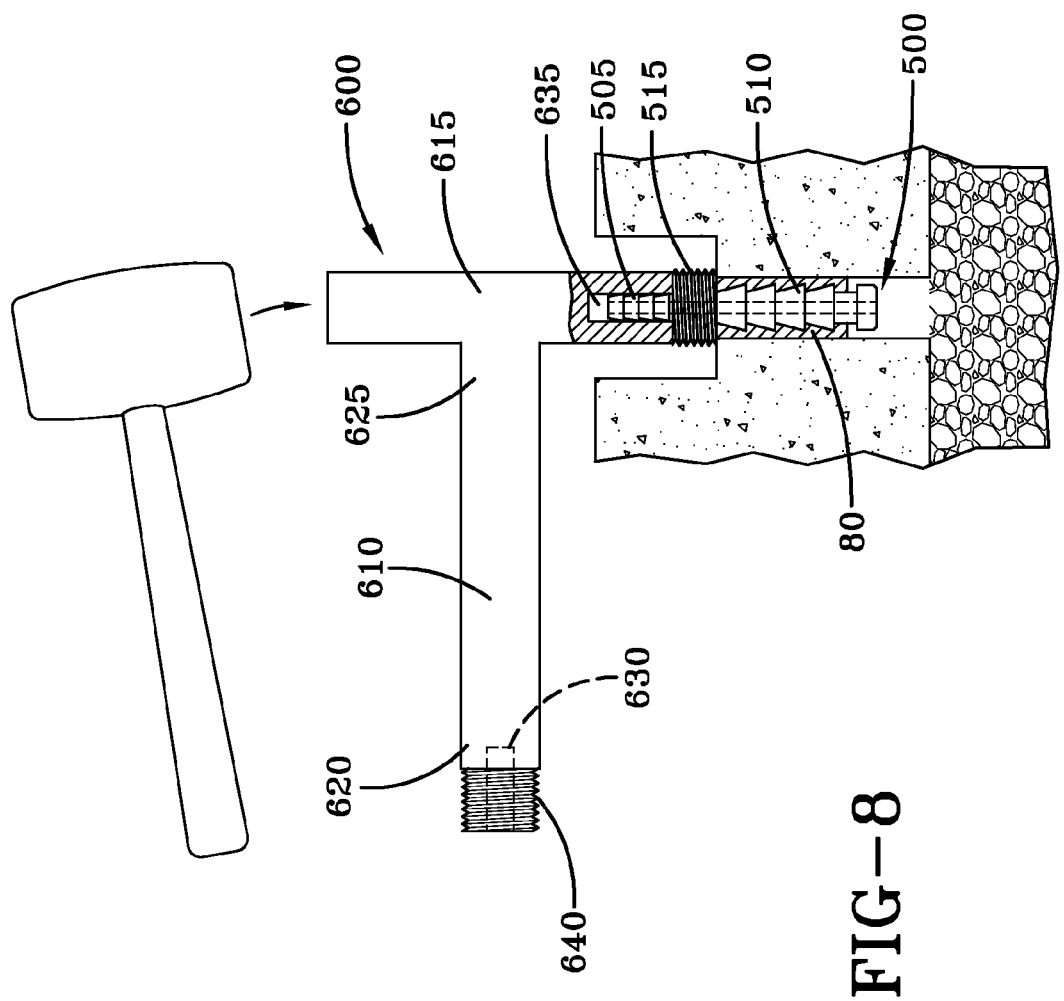
FIG. 8 is a side view of an exemplary tool being used to install an exemplary adaptor tool.

As stated herein, the adaptor body 500 may be installed and extracted using an exemplary embodiment of a tool 600. FIG. 8 illustrates another exemplary tool 600 used for the installation and extraction of the adaptor body 500. As shown, the tool 600 has a T-shaped body. The tool includes a stem portion 610 and a handle portion 615. As shown in FIG. 8, the stem 610 has a first end 620 and second end 625. The second end 625 intersects the handle 615 so that the stem portion 610 extends substantially perpendicular from the handle 615. The first end 620 of the stem portion 610 is threaded and has an extraction cavity 630 therein. The threaded portion 640 of the first end 620 is a predetermined length sufficient for extraction of the adaptor body 500, as will be discussed herein. To install the adaptor body 500, the handle has at least one installation cavity 635 therein. As shown in FIG. 8, the installation cavity 635 is adapted to accommodate the first barbed end 505 of the adaptor body 500.

To install the adaptor body 500 using the tool 600, the first barbed end 505 is inserted into the installation cavity 635 in the handle 615. A mallet or other device is then used to strike the end of the handle 615 opposite of the installation cavity 635 in order to force the adaptor body 500 into the drilled core (as shown in FIG. 8). After installation of the adaptor body 500, the tool 600 is simply removed from the adaptor body 500 and the adaptor body 500 is connected to a soil gas measuring device.

Extraction of the adaptor body 500 is illustrated in FIGS. 9 and 10. The threaded portion 640 of the first end 620 of the stem 610 is threaded into the coupling 700. The coupling 700 is threaded completely onto the pre-determined length of the threaded portion 640. The tool 600 is then used to thread the coupling 700 onto the threaded collar 515 of the adaptor body 500. It should also be understood that the coupling 700 can be threaded onto the adaptor body 500 then the tool 600 may be threaded into the coupling 700.

To extract the adaptor body 500 from the core a user continued to turn the tool 600. Due to the threaded connection between the adaptor body 500 and the coupling 700, the adaptor body 500 is forced upward into the coupling 700. As the adaptor body 500 is raised upward as a result of the rotational motion of the tool 600 the first barbed portion 505 of the adaptor body 500 is inserted into the extraction cavity 630. This enables the adaptor body 500 to be moved upward without the need to readjust the tool 600. Once the threaded collar 515 comes into contact with the first end 620 of the tool 600, the tool 600 can be used to lift the adaptor body 500 from the drilled core.

In still other exemplary embodiments, rather than having a male threaded portion at the first end 620, the first end may have a female threaded portion (not shown in the Figures). The female threaded portion may be sufficiently sized to be threaded onto the threaded collar 515 of the adaptor body 500. In this embodiment, the need for a coupling 700 may be avoided.

While certain embodiments of the present invention are described in detail above, the scope of the invention is not to be considered limited by such disclosure, and modifications are possible without departing from the spirit of the invention as evidenced by the following claims:

What is claimed is:

1. A device for facilitating the analysis of samples of a sub-slab soil gas, comprising:
    an adaptor body, having an internal cavity axially passing therethrough, comprising:
        a first barbed portion, said barbed portion having at least one barb situated at a proximal end of the adaptor body;
        a second barbed portion that includes at least one barb and is located at the distal end of the adaptor body;
        a threaded collar portion interposed between said first and second barbed portions, said threaded collar portion adapted to provide a surface for a tool to contact during installation and removal of the adaptor body, said tool including:
            a stem having a first and second end, the first end having a pre-determined length of male threads located thereon, the second end intersecting with a handle;
            an installation cavity disposed within an at least one end of said handle, said installation cavity adapted to receive said first barbed portion;
            an extraction cavity disposed within the first end of said stem, said extraction cavity adapted to receive said first barbed portion; and
        a tubular body with an interior cavity adapted to receive at least the second barbed portion of the adaptor body to produce a mating engagement therebetween.

2. The device of claim 1, further comprising a raised end on the distal end of the adaptor body.

3. The device of claim 2, wherein the raised end includes a chamfer that facilitates the insertion of the raised end within the inner cavity of the tubular body.

4. The device of claim 1, further comprising an installation tool that is adapted to apply force on a portion of the adaptor body to effectuate installation of the adaptor body within a drilled core.

5. The device of claim 1, wherein said tool is T-shaped.

6. The device of claim 1, wherein said tool further comprises a coupling threaded onto said first end of said stem.

7. A system for facilitating the analysis of samples of a sub-slab soil gas, comprising:
    a tool, said tool including:
        a stem having a first and second end;
        a threaded portion located on at said first end of said stem, said threaded portion having a predetermined length;
        a handle intersecting with said stem at said second end;
        an installation cavity disposed within an at least one end of said handle;
        an extraction cavity disposed within said first end of said stem;
    an adaptor body, said adaptor body including:
        a first and second barbed portion joined by a threaded collar portion;
        an internal cavity that axially passes through the length of the adaptor body; and
        a tubular body with an interior cavity adapted to receive at least the second barbed portion of the adaptor body to produce a mating engagement therebetween.

8. The system of claim 7, further comprising a coupling adapted to thread onto said threaded portion of said tool and said threaded collar of said adaptor body.

9. The system of claim 8, wherein said threaded portion is adapted to engage said threaded collar of said adaptor body.

10. The system of claim 8, wherein said tool is T-shaped.

11. The system of claim 8, further comprising a high friction material, said high friction material used between the intersecting portions of the tubular body and the second barbed portion.

12. The system of claim 8, wherein said installation cavity is adapted to receive said first barbed portion.

13. The system of claim 8, wherein said extraction cavity is adapted to receive said first barbed portion.

14. The system of claim 8, wherein rotational force of the tool is translated to an upward force on said adaptor body for extraction.

15. A method for collecting gas samples of sub-slab soil gas for analysis, comprising:
    providing an adaptor body, said adaptor body comprising a first and second barbed portion and a threaded collar joining said first and second barbed portions;
    providing a tool, said tool comprising a stem having a first and second end, a threaded portion located at the first end, a handle extending from said second end, an installation cavity disposed within an at least one end of said handle, and an extraction cavity disposed within said first end of said stem;
    securing a tubular body around at least a portion of said second barbed portion;
    placing at least a portion of said first barbed portion within said installation cavity in said tool;
    striking said handle opposite said installation cavity in order to force said adaptor body and associated tubular body into a drilled core;
    connecting a soil gas measurement device to said first barbed portion;
    attaching the threaded portion of the first end to the thread collar of the adaptor body;

rotating said tool relative to said adaptor body in order to force said adaptor upward; and inserting at least a portion of said first barbed portion into said extraction cavity.

16. The method of claim 15, wherein said threaded portion of said first end is attached to the threaded collar by a coupling.

17. The method of claim 15, wherein said threaded portion of said first end is threaded directly onto said threaded collar of said adaptor body.

18. The method of claim 15, wherein said tool has a T-shape.

* * * * *